United States Patent
Zhang et al.

(10) Patent No.: US 12,390,433 B2
(45) Date of Patent: Aug. 19, 2025

(54) COMPOSITIONS AND METHODS FOR IMPROVING EXERCISE PERFORMANCE OR PREVENTING OR RELIEVING FATIGUE

(71) Applicant: NANJING NUTRABUILDING BIO-TECH CO., LTD., Nanjing (CN)

(72) Inventors: Qianjing Zhang, Nanjing (CN); Rui Shu, Nanjing (CN); Shawn Wells, Nanjing (CN); Kylin Liao, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 153 days.

(21) Appl. No.: 18/160,417

(22) Filed: Jan. 27, 2023

(65) Prior Publication Data

US 2024/0252460 A1    Aug. 1, 2024

(30) Foreign Application Priority Data

Jan. 28, 2022 (WO) ................ PCT/CN2022/074622

(51) Int. Cl.
*A61K 31/197* (2006.01)
*A61P 3/02* (2006.01)
*A61P 43/00* (2006.01)

(52) U.S. Cl.
CPC .............. *A61K 31/197* (2013.01); *A61P 3/02* (2018.01); *A61P 43/00* (2018.01)

(58) Field of Classification Search
CPC ........... A61K 31/197; A61P 3/02; A61P 43/00
See application file for complete search history.

(56) References Cited

U.S. PATENT DOCUMENTS 8,466,198 B2 * 6/2013 Kneller ................ C07C 279/14
514/564

FOREIGN PATENT DOCUMENTS

CA         2746922 A1 *  1/2012  ............. A61K 36/00
WO    WO-2016179657 A1 * 11/2016  ........... A23L 33/175

OTHER PUBLICATIONS

Tanianskii, D.A.; Jarzebska, N.; Birkenfeld, A.L.; O'Sullivan, J.F.; Rodionov, R.N. Beta-Aminoisobutyric Acid as a Novel Regulator of Carbohydrate and Lipid Metabolism. Nutrients 2019, 11, 524. (Year: 2019).*
Zabihi, Mohsen, et.al., Ascorbic Acid Significantly Decreases Creatine Kinase Plasma Levels in an Animal Model of Statin/ Fibrate-Induced Myopathy, Advances in Pharmacological and Pharmaceutical Sciences, 2021, 5539595, 7 pages, 2021. (Year: 2021).*
Lo, H., et al. "Effects of postexercise supplementation of chicken essence on the elimination of exercise-induced plasma lactate and ammonia." Chinese Journal of Physiology 48.4 (2005): 187. (Year: 2005).*
Roberts, Lee D., et al. "$\beta^2$-Aminoisobutyric acid induces browning of white fat and hepatic $\beta^2$-oxidation and is inversely correlated with cardiometabolic risk factors." Cell metabolism 19.1 (2014): 96-108.) (Year: 2014).*

* cited by examiner

*Primary Examiner* — James H Alstrum-Acevedo
*Assistant Examiner* — Justin Christopher Sanchez
(74) *Attorney, Agent, or Firm* — ANOVA LAW GROUP, PLLC

(57) ABSTRACT

The present invention provides a method for improving exercise performance or preventing or relieving fatigue in mammal, including administration to the mammal a composition including: (i) an effective amount of BAIBA, or a pharmaceutically acceptable salt, acid, ester, polymer, analog or derivative thereof; and (ii) an effective amount of creatine. The present invention also provides a composition, including (i) an effective amount of BAIBA, or a pharmaceutically acceptable salt, acid, ester, polymer, analog or derivative thereof; and (ii) an effective amount of creatine, for improving exercise performance or preventing or relieving fatigue in a mammal. The methods and compositions of the invention can be used for enhancing muscle strength, increasing muscle content, improving muscle endurance; preventing body fatigue after exercise, accelerating recovery after exercise.

8 Claims, No Drawings

COMPOSITIONS AND METHODS FOR IMPROVING EXERCISE PERFORMANCE OR PREVENTING OR RELIEVING FATIGUE

CROSS REFERENCE TO RELATED APPLICATION

This application claims the benefit of a PCT International Application Number PCT/CN2022/074622, filed on Jan. 28, 2022, the content of which is hereby incorporated by reference in its entirety for all purposes.

FIELD OF THE INVENTION

The present invention belongs to the technical field of health food and dietary supplements; specifically, relates to compositions and methods for improving exercise performance or preventing or relieving fatigue, especially enhancing muscle strength, increasing muscle content, improving muscle endurance; or preventing body fatigue after exercise, accelerating recovery after exercise, in a mammal.

BACKGROUND OF THE INVENTION

People who carry out sports, especially high strength sports or participate in bodybuilding need special diet to improve their muscle strength or increase their muscle mass.

Muscle contraction depends upon the hydrolysis of adenosine triphosphate (ATP), which releases free energy when a phosphate bond is broken. Three systems function to supply energy in the form of ATP to muscle—the phosphagen system, glycolysis, and mitochondrial respiration.

Methods of administrating certain supplements that help any one of these three systems may be helpful for improving exercise performance or preventing or relieving fatigue, especially enhancing muscle strength, increasing muscle content, improving muscle endurance; or preventing body fatigue after exercise, accelerating recovery after exercise.

SUMMARY OF THE INVENTION

In a first aspect, the present invention provides a method for improving exercise performance or preventing or relieving fatigue in a mammal, comprising administration to the mammal a composition comprising: (i) an effective amount of BAIBA, or a pharmaceutically acceptable salt, acid, ester, polymer, analog or derivative thereof; and (ii) an effective amount of creatine.

In some embodiments, the improving exercise performance includes enhancing muscle strength, increasing muscle content, improving muscle endurance; the preventing or relieving fatigue includes preventing body fatigue after exercise, accelerating recovery after exercise.

In some embodiments, the improving exercise performance or preventing or relieving fatigue is achieved through reducing blood ammonia, lactate, creatine kinase.

In some embodiments, the composition is administrated in a form of an aqueous solution, aqueous suspension, capsule, drop, granule, liquid, powder, syrup, tablet, functionalized food, beverage, toothpaste, or sublingual articles.

In some embodiments, the BAIBA, or a pharmaceutically acceptable salt, acid, ester, polymer, analog or derivative thereof is administered in an amount of 100 mg-2500 mg/day; the creatine is administered in an amount of 0.5 g-10 g/day. In some embodiments, the BAIBA, or a pharmaceutically acceptable salt, acid, ester, polymer, analog or derivative thereof is administered in an amount of 50 mg-5000 mg/day, preferably 60 mg-3500 mg/day, more preferably 100 mg-2500 mg/day, most preferably 500 mg-1500 mg/day. In some embodiments, the creatine is administered in an amount of 0.1 g-10 g/day, preferably 0.5 g-10 g/day, more preferably 1 g-6 g/day, most preferably 3 g-5 g/day.

In some embodiments, the composition is formulated into nutritional supplement, food, beverage, animal feed or medicine.

In some embodiments, the administration is through various routes selected from oral administration, intravenous injection, intramuscular injection, intraperitoneal injection, topical application, or sublingual application. In some embodiments, the administration is at least once a day or more times a day.

In some embodiments, the mammal is human.

In a second aspect, the present invention provides a composition, comprising (i) an effective amount of BAIBA, or a pharmaceutically acceptable salt, acid, ester, polymer, analog or derivative thereof, and (ii) an effective amount of creatine, for improving exercise performance or preventing or relieving fatigue in a mammal.

In some embodiments, the improving exercise performance includes enhancing muscle strength, increasing muscle content, improving muscle endurance; the preventing or relieving fatigue includes preventing body fatigue after exercise, accelerating recovery after exercise.

In some embodiments, the improving exercise performance or preventing or relieving fatigue is achieved through reducing blood ammonia, lactate, creatine kinase.

In some embodiments, the composition is administrated in a form of an aqueous solution, aqueous suspension, capsule, drop, granule, liquid, powder, syrup, tablet, functionalized food, beverage, toothpaste, or sublingual articles.

In some embodiments, the BAIBA, or a pharmaceutically acceptable salt, acid, ester, polymer, analog or derivative thereof is administered in an amount of 100 mg-2500 mg/day; the creatine is administered in an amount of 0.5 g-10 g/day. In some embodiments, the BAIBA, or a pharmaceutically acceptable salt, acid, ester, polymer, analog or derivative thereof is administered in an amount of 50 mg-5000 mg/day, preferably 60 mg-3500 mg/day, more preferably 100 mg-2500 mg/day, most preferably 500 mg-1500 mg/day. In some embodiments, the creatine is administered in an amount of 0.1 g-10 g/day, preferably 0.5 g-10 g/day, more preferably 1 g-6 g/day, most preferably 3 g-5 g/day.

In some embodiments, the composition is formulated into nutritional supplement, food, beverage, animal feed or medicine.

In some embodiments, the administration is through various routes selected from oral administration, intravenous injection, intramuscular injection, intraperitoneal injection, topical application, or sublingual application. In some embodiments, the administration is at least once a day or more times a day.

In some embodiments, the mammal is human.

In a third aspect, the present invention provides use of a composition for preparing nutritional supplement, food, beverage, animal feed or medicine for improving exercise performance or preventing or relieving fatigue in a mammal, wherein the composition comprises (i) an effective amount of BAIBA, or a pharmaceutically acceptable salt, acid, ester, polymer, analog or derivative thereof; and (ii) an effective amount of creatine.

In some embodiments, the improving exercise performance includes enhancing muscle strength, increasing muscle content, improving muscle endurance; the preventing or relieving fatigue includes preventing body fatigue after exercise, accelerating recovery after exercise.

In some embodiments, the improving exercise performance or preventing or relieving fatigue is achieved through reducing blood ammonia, lactate, creatine kinase.

In some embodiments, the BAIBA, or a pharmaceutically acceptable salt, acid, ester, polymer, analog or derivative thereof is administered in an amount of 100 mg-2500 mg/day; the creatine is administered in an amount of 0.5 g-10 g/day. In some embodiments, the BAIBA, or a pharmaceutically acceptable salt, acid, ester, polymer, analog or derivative thereof is administered in an amount of 50 mg-5000 mg/day, preferably 60 mg-3500 mg/day, more preferably 100 mg-2500 mg/day, most preferably 500 mg-1500 mg/day. In some embodiments, the creatine is administered in an amount of 0.1 g-10 g/day, preferably 0.5 g-10 g/day, more preferably 1 g-6 g/day, most preferably 3 g-5 g/day.

In some embodiments, the composition is administered in a form of an aqueous solution, aqueous suspension, capsule, drop, granule, liquid, powder, syrup, tablet, functionalized food, beverage, toothpaste, or sublingual articles.

In some embodiments, the administration is through various routes selected from oral administration, intravenous injection, intramuscular injection, intraperitoneal injection, topical application, or sublingual application. In some embodiments, the administration is at least once a day or more times a day.

In some embodiments, the mammal is human.

These and other features, aspects, and advantages of the present invention will become better understood with reference to the following description and appended claims.

DETAILED DESCRIPTION OF THE INVENTION

In the Summary Section above and the Detailed Description Section, and the claims below, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Creatine is mainly synthesized in the kidney and liver from the amino acids L-arginine, glycine, and L-methionine. Most of the creatine in the human body is stored in skeletal muscle. The phosphagen system is a form of anaerobic metabolism that uses creatine phosphate to generate ATP, which supports activity for about 10 seconds and enable the athletes to complete a short period of high-intensity exercise, such as the 100 dashes, lifting weights, and so on. Creatine is a substance that turns into creatine phosphate in the body. Supplementing creatine to human increases the phosphocreatine stores in the muscles, which produce more ATP during high-intensity exercise. Supplementing creatine to human also leads to gains in lean muscle mass and enhances power and strength.

Another system that supplies energy in the form of ATP to muscle is glycolysis. The energy for glycolysis comes from glucose or glycogen, the stored form of glucose. Glycogen is a form of carbohydrate that your body stores in your muscles and liver. During exercise, especially high-intensity exercise, muscle glycogen is broken down to produce glucose, which in turn produces ATP, contributing to sports and exercise. Muscle glycogen can be defined as the main fuel source of skeletal muscle tissue during strenuous exercise (such as weightlifting, weightlifting, strongman and competitive fitness, and other sports training). Low levels of muscle glycogen have been repeatedly proven to be one of the key physiological factors that leads to increased fatigue during strenuous exercise, and even plays a role in maintaining strict anaerobic exercise capacity.

BAIBA is a non-protein amino acid secreted by skeletal muscles upon regular exercise via peroxisome proliferator-activated receptor gamma coactivator 1-alpha (PGC-1α)-dependent mechanism. There are two enantiomers of BAIBA in biological systems: D-BAIBA and L-BAIBA. L-BAIBA is generated from catabolic reactions of branched-chain amino acid L-valine, D-BAIBA is produced in the cytosol from thymine in a metabolic pathway. BAIBA has been discovered as a novel endogenous protective myokine regulating adipose tissue browning, improving insulin sensitivity, and protecting against high-fat diet-induced obesity. Many researchers have reported that BAIBA decreases body fat mass, improves glucose tolerance and insulin sensitivity in mice without changing food intake.

Since both BAIBA and creatine play an important role to supply energy in the form of ATP, the inventors of this invention believe that supplementing the combination of BAIBA and creatine can significantly enhance athletes' performance, prevent and relieve the body fatigue caused by exercise.

Terms and phrases used in this application, and variations thereof, especially in the appended claims, unless otherwise expressly stated, should be construed as open ended as opposed to limiting.

As used herein, the term "or" is meant to include both "and" and "or." In other words, the term "or" may also be replaced with "and/or."

As used herein, the singular forms "a," "an" and "the" are intended to include the plural forms as well, unless the context clearly indicates otherwise.

As used herein, the term "comprise" or "include" and their conjugations, refer to a situation wherein said terms are used in their non-limiting sense to mean that items following the word are included, but items not specifically mentioned are not excluded. It also encompasses the more limiting verb 'to consist essentially of' and 'to consist of'.

As used herein, the term "mammal" or "subject" may be used interchangeably to refer to any animal to which the presently disclosed methods and compositions may be applied or administered. The animal may have an illness or other disease, but the animal does not need to be sick to benefit from the presently disclosed methods and compositions. As such any animal may apply the disclosed compositions, or be a recipient of the disclosed methods. "Mammal" includes, without limitation, mice, rats, rabbits, guinea pigs, dogs, cats, sheep, goats, cows, horses, primates, such as monkeys, chimpanzees, and apes, and, in particular, humans. Although the animal subject is preferably a human, the methods and compositions of the invention have application in veterinary medicine.

As used herein, the term "administration" refers to the process of delivering a disclosed composition or active ingredient to a subject. The compositions of the invention can be administered in a variety of ways, including orally, intragastrically, and parenterally (e.g., intravenous and intraarterial as well as other suitable parenteral routes), and the like, so as to exert the desired effects.

As used herein, an "effective amount" refers to a sufficient amount of BAIBA and creatine, at a reasonable benefit/risk ratio applicable to improving exercise performance or preventing or relieving fatigue, especially enhancing muscle strength, increasing muscle content, improving muscle endurance, or preventing body fatigue after exercise, accelerating recovery after exercise. It will be understood, however, that the total daily usage of BAIBA and creatine may be decided by the attending physician or personal coach within the scope of sound medical judgment. The specific effective dose level for any particular subject will depend upon a variety of factors including the signs being treated and the severity of the signs; the specific composition employed; the age, body weight, general health, sex and diet of the subject; the time of administration, route of administration, and rate of excretion of BAIBA and creatine employed; the duration of the administration; drugs used in combination or coincidental with BAIBA and creatine; and like factors well known in the medical arts or sports science. In addition, an "effective amount" is the amount that will elicit the biological or medical response of a tissue, system, or subject.

One of skill in the art recognizes that an amount may be considered "effective" even if the condition is not totally eradicated or prevented, but it or its symptoms and/or effects are improved or alleviated partially in the subject. Various indicators for determining the effectiveness of a method are known to those skilled in the art for improving exercise performance, or preventing or relieving fatigue in a mammal.

As used herein, the term "pharmaceutically acceptable" means pharmaceutically, physiologically, alimentarily, and/or nutritionally acceptable, and refers to those compositions or combinations of agents, materials, or compositions, and/or their dosage forms, which are within the scope of sound medical judgment, suitable for use in contact with the tissues of human beings and animals without excessive toxicity, irritation, allergic response, or other problem or complication, commensurate with a reasonable benefit/risk ratio.

Other ingredients may be included in the claimed composition, such as other active agents, preservatives, buffering agents, salts, a pharmaceutically acceptable carrier, or other pharmaceutically acceptable ingredients.

In some embodiments, the composition comprises from about 5% to about 10%, 20%, 30%, 40%, 50%, 60%, 70%, 80%, 90%, or 95% by weight of BAIBA and creatine, and preferably from about 30% to about 90% by weight of BAIBA and creatine, based upon the total weight of the composition taken as 100% by weight.

In some embodiments, BAIBA is administered in an amount of 100 mg/day-2500 mg/day. In some embodiments, BAIBA is administered in an amount of 500 mg/day-1500 mg/day.

In some embodiments, creatine is administered in an amount of 0.5 g/day-10 g/day. In some embodiments, creatine is administered in an amount of 3 g/day-5 g/day. In some embodiments, creatine is administered at about 0.1 g/kg of body weight per day.

The dosage may range broadly, depending upon the desired effects and the indication. The daily dosage regimen for an adult human patient may be, for example, an oral dose of between 0.01 mg and 3000 mg of BAIBA and creatine, preferably between 1 mg and 700 mg, e.g., 5 to 200 mg, or between about 0.1 mg and about 1,000 mg of BAIBA and creatine per kg of body weight of the subject. The dosage may be a single one or a series of two or more given in the course of one or more days, as is needed by the subject. In some embodiments, the compounds are administered for a period of continuous therapy, for example for a week or more, or for months or years.

In some embodiments, the combination supplement is administrated in a form of an aqueous solution, aqueous suspension, capsule, drop, granule, liquid, powder, syrup, tablet, functionalized food, beverage, toothpaste, or sublingual articles.

In some embodiments, the composition is prepared in a form of pharmaceutical composition.

The term "pharmaceutical composition" refers to a mixture of BAIBA and creatine with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration. A pharmaceutical composition is suitable for human and/or veterinary applications.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

As used herein, a "carrier" refers to a compound that facilitates the incorporation of a compound into cells or tissues. For example, without limitation, dimethyl sulfoxide (DMSO), Ethanol (EtOH), or PEG400 is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes.

Any titles or subheadings used herein are for organization purposes and should not be used to limit the scope of embodiments disclosed herein.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for.

All publications and patent applications cited in this specification are herein incorporated by reference as if each individual publication or patent application were specifically and individually indicated to be incorporated by reference.

EXAMPLES

Mice were divided into four groups, one group was BAIBA group, supplementing 100 mg/kg. body weight (b. w.) BAIBA; one group was creatine group, supplementing 200 mg/kg b. w. creatine; one group was BAIBA with creatine group, supplementing 100 mg/kg. b. w. BAIBA and 200 mg/kg b.w. creatine; one group was blank control group, supplementing nothing but diet. All mice were fed a normal diet. Four groups were fed according to the above protocol for 4 weeks.

Example 1

The average weight of mice in each group was measured by weighing scale before supplementation and after 4 weeks of supplementation, and the data were recorded in Table 1. As shown in Table 1, the application of creatine will increase the body weight, while the application of BAIBA and creatine can help to control body weight.

TABLE 1

Body weight (g) of mice in each group

| Group | Baseline | Week 4 |
|---|---|---|
| BAIBA | 29.71 | 25.41 |
| Creatine | 27.59 | 27.65 |
| BAIBA + Creatine | 28.11 | 23.55 |
| Control | 28.45 | 29.88 |

Example 2

The forelimb grip strength of mice in each group was measured by grip strength meter before supplementation and after 4 weeks of supplementation. Each of the mice was placed on the experimental table, and grab bar with force sensor was placed in front of the head. When the tail of the mouse was dragged by the experimenter, the mouse would instinctively grasp the grab bar in front thereof to prevent the unintentional backward movement until the experimenter's pulling force exceeds its grip strength upper limit. When the grab bar was released, the instrument would automatically record the grip strength upper limit value and display it on the LCD screen, and the data were recorded in Table 2. As shown in Table 2, the application of BAIBA and creatine can obviously increase the forelimb grip strength, which indicates that the supplement of BAIBA and creatine can effectively enhance muscle strength.

TABLE 2

Forelimb grip strength (kg) of mice in each group

| Group | Baseline | Week 4 |
|---|---|---|
| BAIBA | 0.15 | 0.17 |
| Creatine | 0.14 | 0.19 |

TABLE 2-continued

Forelimb grip strength (kg) of mice in each group

| Group | Baseline | Week 4 |
|---|---|---|
| BAIBA + Creatine | 0.14 | 0.21 |
| Control | 0.15 | 0.16 |

Example 3

After 4 weeks of supplementation, a 150 cm×60 cm×60 cm glass pool with a water depth of 45~50 cm was selected for exhaustive swimming experiment of mice in each group. During training, the mice that didn't swim were driven away with wooden sticks to ensure a certain load. Exhaustion standard: The swimming movement was obviously out of balance, and the mouse couldn't persist any more, and it couldn't return to the water surface after sinking underwater for 5 s. Exhaustive swimming time: the time from the beginning of swimming to the first time that the mouse's nostril sank to the water surface, and the data were recorded in Table 3. As shown in Table 3, the application of BAIBA and creatine can greatly prolong the exhaustive swimming time of mice, which indicates that the supplementation of BAIBA and creatine can significantly improve muscle endurance.

TABLE 3

Exhaustive swimming time (min) of mice in each group

| Group | Week 4 |
|---|---|
| BAIBA | 9.79 |
| Creatine | 13.03 |
| BAIBA + Creatine | 16.54 |
| Control | 6.45 |

Example 4

The contents of gastrocnemius and soleus muscle of mice in each group were measured by awake animal body composition analyzer before supplementation and after 4 weeks of supplementation, and the data were recorded in Table 4. As shown in Table 4, the application of BAIBA and creatine can significantly increase the contents of both gastrocnemius and soleus, which indicates that the supplementation of BAIBA and creatine can significantly increase muscle content.

TABLE 4

Muscle content (%) of mice in each group

| | Baseline | | Week 4 | |
|---|---|---|---|---|
| Group | Gastrocnemius | Soleus | Gastrocnemius | Soleus |
| BAIBA | 5.14 | 3.12 | 30.25 | 25.14 |
| Creatine | 4.63 | 3.95 | 45.12 | 33.25 |
| BAIBA + Creatine | 6.44 | 4.68 | 74.15 | 52.49 |
| Control | 5.81 | 5.01 | 9.21 | 8.15 |

Example 5

The tail tip blood of each mouse was taken after acute swimming, before supplement and after 4 weeks of supplementation, and the serum was extracted by centrifugation. The levels of creatine kinase, blood ammonia, blood lactic acid and blood sugar in the serum were measured by commercial kits according to instructions, and the data were respectively recorded in Tables 5-8. As shown in Tables 5-7, the application of BAIBA and creatine can significantly control the content of creatine kinase, and effectively reduce the levels of blood ammonia and lactate, which indicates that the supplementation of BAIBA and creatine can effectively improve exercise

TABLE 5

Creatine kinase (IU/L) of mice in each group

| Group | Baseline | Week 4 |
|---|---|---|
| BAIBA | 245.11 | 639.79 |
| Creatine | 278.15 | 583.03 |
| BAIBA + Creatine | 304.21 | 516.54 |
| Control | 258.56 | 949.13 |

TABLE 6

Blood ammonia (μM) of mice in each group

| Group | Baseline | Week 4 |
|---|---|---|
| BAIBA | 111.18 | 170.89 |
| Creatine | 105.95 | 159.74 |
| BAIBA + Creatine | 99.56 | 115.61 |
| Control | 108.12 | 232.47 |

TABLE 7

Blood lactate (mM) of mice in each group

| Group | Baseline | Week 4 |
|---|---|---|
| BAIBA | 2.56 | 8.12 |
| Creatine | 2.95 | 6.48 |
| BAIBA + Creatine | 3.01 | 5.89 |
| Control | 2.89 | 17.51 |

TABLE 8

Blood glucose (mg/dL) of mice in each group

| Group | Baseline | Week 4 |
|---|---|---|
| BAIBA | 138 | 121 |
| Creatine | 149 | 135 |
| BAIBA + Creatine | 152 | 129 |
| Control | 143 | 104 |

As shown in the above examples, the supplementation of BAIBA+creatine can effectively enhance muscle strength, significantly improve muscle endurance, and significantly increase muscle content, thus contributing to the improvement of exercise performance. The supplementation of BAIBA+creatine can also significantly control creatine kinase content, effectively reduce blood ammonia and blood lactate levels, thus helping to improve exercise performance, and also helping to prevent or relieve fatigue, such as preventing body fatigue after exercise or accelerating recovery after exercise. In addition, the supplement of BAIBA+creatine can effectively control body weight and prevent hypoglycemia.

Although specific embodiments and examples of this invention have been illustrated herein, it will be appreciated by those skilled in the art that any modifications and variations can be made without departing from the spirit of the invention. The examples and illustrations above are not intended to limit the scope of this invention. Any combination of embodiments of this invention, along with any obvious their extension or analogs, are within the scope of this invention. Further, it is intended that this invention encompass any arrangement, which is calculated to achieve that same purpose, and all such variations and modifications as fall within the scope of the appended claims.

What is claimed is:

1. A method for improving exercise performance or preventing or relieving fatigue in a mammal, comprising administration to the mammal a composition comprising: (i) an effective amount of BAIBA, or a pharmaceutically acceptable salt, acid, ester, or polymer thereof; and (ii) an effective amount of creatine.

2. The method of claim 1, wherein improving exercise performance includes enhancing muscle strength, increasing muscle content, improving muscle endurance; and preventing or relieving fatigue includes preventing body fatigue after exercise, accelerating recovery after exercise.

3. The method of claim 1, wherein improving exercise performance or preventing or relieving fatigue is achieved through reducing blood ammonia, lactate, creatine kinase.

4. The method of claim 1, wherein the composition is administrated in a form of an aqueous solution, aqueous suspension, capsule, drop, granule, liquid, powder, syrup, tablet, functionalized food, beverage, toothpaste, or sublingual articles.

5. The method of claim 1, wherein the BAIBA, or a pharmaceutically acceptable salt, acid, ester, polymer, analog or derivative thereof is administered in an amount of 100 mg-2500 mg/day; the creatine is administered in an amount of 0.5 g-10 g/day.

6. The method of claim 1, wherein the composition is formulated into nutritional supplement, food, beverage, animal feed or medicine.

7. The method of claim 1, wherein the administration is through various routes selected from oral administration, intravenous injection, intramuscular injection, intraperitoneal injection, topical application, or sublingual application.

8. The method of claim 1, wherein the mammal is human.

* * * * *